United States Patent [19]

Baer et al.

[11] 4,014,991
[45] Mar. 29, 1977

[54] ORAL RABIES IMMUNIZATION OF CARNIVORES

[75] Inventors: George M. Baer; William G. Winkler, both of Stone Mountain, Ga.

[73] Assignee: The United States of America as represented by the Department of Health, Education and Welfare, Washington, D.C.

[22] Filed: Jan. 23, 1976

[21] Appl. No.: 651,810

[52] U.S. Cl. .................................. 424/89; 424/84
[51] Int. Cl.² ...................................... A61K 39/28
[58] Field of Search .............................. 424/84, 89

[56] References Cited
UNITED STATES PATENTS 3,046,192   7/1962   Bilyeu ................................ 424/84

*Primary Examiner*—Sam Rosen
*Attorney, Agent, or Firm*—John S. Roberts, Jr.; Norman J. Latker; Thomas G. Ferris

[57] ABSTRACT

A vaccine and method of protecting wild carnivores and especially foxes from rabies virus which comprises setting out and orally administering an immunizing dose of an attenuated liquid antirabies vaccine, said vaccine being enclosed in a bite-permeable hydrophobic plastic container or sheath and said container being surrounded by an acceptable meat bait for the carnivore such as cured sausage. An elongated shape for both the container and bait is preferred. Acceptable vaccines for utilization include ERA/BHK-21 and PRI virus and a plastic elongated polyethylene tube is preferred for the container holding the attenuated vaccine. An effective amount of a temperature stabilizer for the vaccine may be added for operating temperatures of 27°⁺C. and these temperature stabilizers are selected from purified casein hydrolysates. The present method operates by bite penetration of the plastic container so that the vaccine is transferred to the buccal mucosa of the carnivore and the present method is effective in the treatment of wild carnivores, especially foxes.

18 Claims, No Drawings

ORAL RABIES IMMUNIZATION OF CARNIVORES

The control of rabies in terrestrial animal life and especially in wild carnivores, such as the fox, is integral to the ultimate goal of minimizing the public health significance of this disease in the United States. Since population reduction in the past has not proved an effective animal wildlife rabies control technique, vaccination of carnivores has received increasing interest in recent years.

The present invention relates to vaccine and a method of protecting wild carnivores and especially foxes from rabies virus which comprises setting out and orally administering an immunizing dose of an attenuated liquid antirabies vaccine, said vaccine being enclosed in a bite-permeable hydrophobic plastic container or sheath and said container being surrounded by an acceptable meat bait for the carnivore such as cured sausage. An elongated shape for both the container and bait is preferred. Acceptable vaccines for utilization include ERA/BHK-21 and PRI virus and a plastic elongated polyethylene tube is preferred for the container holding the attenuated vaccine. An effective amount of a temperature stabilizer for the vaccine may be added for operating temperatures of 27°+ C. and these temperature stabilizers are selected from purified casein hydrolysates. The present method operates by bite penetration of the plastic container so that the vaccine is transferred to the buccal mucosa of the carnivore and the present method is effective in the immunization of wild carnivores, especially foxes.

PRIOR ART

As contrasted to the present invention, set out below is a statement of known prior art.

Patents

U.S. Pat. No. 3,228,840 Macpherson et al. — Virus culture utilizing clone 13 of the BHK-21 hamster strain denoted ATCC accession number CL 10.

U.S. Pat. No. 3,423,505 Crawley et al. — Teaches the product of the ERA strain of rabies virus ATCC VR 332, which is propagated in live kidney cells and is substantially free from viral or bacterial contaminants.

U.S. Pat. No. 3,585,266 Emery et al. — A live modified rabies virus produced by tissue culture technique employing bovine kidney cells to increase antigenicity.

U.S. Pat. No. 3,629,390 Wentworth — Population control of birds by oral vaccination is set out at column 4, lines 9–18.

U.S. Pat. No. 3,823,228 Ferris et al. — The oral administration of enteric-coated particles as vaccine for TGE in the protection of swine.

Literature

Black and Lawson, "Further Studies of Sylvatic Rabies in the Fox (*Vulpes Vulpes*), Vaccination by the Oral Route," Can. Vet. Jour., 14(9), September, 1973, pages 206–211. The authors orally vaccinate foxes, both silver and red varieties, utilizing the ERA strain of rabies virus grown in BHK-21 cells into the buccal cavity. The virus utilized in this case was reconstituted or freeze-dried type and specially set out as free choice in Tables V and VI (page 209). The use of bait is mentioned with regard to the studies in these tables but no definition is given as to the type of bait.

Baer et al., "Oral Vaccination of Foxes Against Rabies," Am. J. Epid., 93(6), 1971, pages 487–490. An earlier method of oral vaccination of grey and red foxes by various methods such as stomach tube, feeding explosion using a "coyote-getter," and other methods. No baits were utilized.

Debbie et al., "The Use of Commercially Available Vaccines for the Oral Vaccination of Foxes Against Rabies," Am. J. Epid., 96(3), 1972, pages 231–235. In this prior art article, including one of the present inventors, it was demonstrated that as to wild red foxes (*Vulpes fulva*), successful vaccination was achieved by utilization of ERA virus with a titer $\geq 10^{3.4}$ MICLD$_{50}$/0.03 ml.

Abelseth, "An Attenuated Rabies Vaccine for Domestic Animals Produced in Tissue Culture," Can. Vet. Jour., vol. 5, November 1964, pages 279–286.

The principle differences of the present vaccine and method of protecting carnivores are:

1. The present use of a liquid vaccine rather than a reconstituted or freeze-dried vaccine in the combination, which vaccine retains a high titer at relatively high ambient temperatures of about 35° C with a stabilizer.

2. The utilization of a polymeric sheath preferably elongated or pencil-shaped which will carry an immunizing dosage of rabies vaccine. This polymeric sheath or container is hydrophobic so that the liquid vaccine will not leak to the outside and is also bite permeable so that the vaccine can be released from the interior of the container to be lodged in the mouth or buccal mucosa of a carnivore, such as a fox. A preferred material is a clear or colored polyethylene or polypropylene sheath container.

3. A further novel development is surrounding the enclosed vaccine with a meat bait attractive to the carnivore such as a fox. A cured sausage is preferred, such as the conventional Slim Jim, but other meats such as hamburger may be utilized.

In the present procedure the bait vaccine is set out for the fox or other wild carnivore and the fox receives the vaccine by biting through and penetrating the polymeric sheath and thus, by rupturing, places the vaccine in contact with the tongue and the buccal mucosa. The bite penetration of the plastic container releases an immunizing dose of the vaccine into the tongue and cheek mucosa and buccal cavity of the fox who is thus immunized subsequently against rabies virus.

THE COMBINATION OF THE VACCINE AND CONTAINER

In the present development and its utilization with a bait, there came principally a finding that liquid vaccine could be stabilized within a suitable and acceptable device. It was known that ERA vaccine could be grown on BHK cells and is an effective agent for immunizing foxes against rabies by the oral route. The ERA vaccine is an attenuated virus and a minimum titer is required to assure its replication on the tongue and cheek mucosa, thus resulting in the subsequent development of neutralizing antibodies. Since a minimum titer of $10^{4.0}$ mouse intracerebral LD$_{50}$ (MICLD$_{50}$) is necessary to vaccinate foxes, a highly susceptible species, it seemed necessary to require an initial titer of $10^{6.0}$ or more to thus assure a sufficient titer even after an expected decrease of up to 2 logarithms of virus ($10^2$) in field. To obtain this minimum, there was used BHK cells grown at 37° C in roller bottles in Eagles minimum essential growth medium for 5 days (*Virology*, 16:147–151, 1962). The growth medium was then discarded, the cells seeded with commercial ERA vaccine, and a virus medium was added to provide for maximum virus replication. A modified Basal Medium (Eagle) is set out as Example 2. The infected roller bottles were then rotated at 32° C for a further 5 days and the supernatant liquid was harvested. A virus titer of $10^{6.5}$ to $10^{7.5}$ MICLD$_{50}$ routinely resulted. At 35°–37° C a drop to almost nil is noted in 48 hours:

TABLE 1

| Stability of ERA-BHK at 37° C | |
|---|---|
| Pre-Incubation | $10^{6.5}$ |
| Post Incubation | |
| 24 hr. | $10^{4.0}$ |
| 48 hr. | $10^{0.3}$ |
| 72 hr. | $< 10^{1.0}$ |
| 96 hr. | $< 10^{1.0}$ |

As a result of the observations at slightly elevated temperatures and the drop of virus titer, the stabilizers are added to the vaccine produced to achieve temperature stabilization. In the experiments of surrounding the liquid form of the vaccine in preferred Slim Jim solid smoked meat sausages, a dialysis membrane was first used to separate the vaccine from the meat but toxic factors apparently entered from the meat and the titer of the vaccine dropped rapidly as shown in the following Table 2:

TABLE 2

| | |
|---|---|
| Pre-Incubation | $10^{6.8}$ |
| Day 1 | $10^{5.7}$ |
| Day 2 | $10^{2.3}$ |
| Day 3 | $<10^{1.0}$ |

However, when a more solid and hydrophobic container was utilized, such as a simple plastic polyethylene straw, the titer of the vaccine bore up quite well even at 35° C and again these results are set out in Table 3 below:

TABLE 3

| | |
|---|---|
| Pre-Incubation | $10^{6.3}$ |
| Day 1 | $10^{5.5}$ |
| Day 2 | $10^{4.3}$ |
| Day 3 | $10^{4.5}$ |

STABILIZERS

The present liquid vaccine, through the addition of suitable amounts of a stabilizer which stabilizes the vaccine according to temperature, cannot only be utilized at room temperature of 20° C but the temperatures in warm climates approaching 35° C. The temperature stabilizer for the vaccine is selected from a group of highly purified casein hydrolysates. Especially satisfactory have been such stabilizers as N Z Amine AS, N Z Amine HD, and N Z Case M (Sheffield Chemical, Union, New Jersey). These hydrolysates are water soluble and have been found to effectively preserve the titer of the vaccines produced here, such as ERA/BHK virus, for at least a 3-day post-incubation period. A summary of the results as to this aspect are set out in the table below:

TABLE 4

| ERA-BHK Virus Mixed with Different Reagents | | | |
|---|---|---|---|
| Pre-Incubation Titer $10^{-5.7}$ | | | |
| | 27° C | 35° C | |
| 1 day Post Incubation | $10^{-5.5}$ | $10^{-4.7}$ | N Z Amine AS |
| 3 day Post Incubation | $10^{-5.3}$ | $10^{-4.3}$ | 210 g/1000 cc |
| 1 day Post Incubation | $10^{-5.8}$ | $10^{-4.8}$ | N Z Amine HD |
| 3 day Post Incubation | $10^{-5.3}$ | $10^{-4.3}$ | 200 g/1000 cc |
| 1 day Post Incubation | $10^{-5.2}$ | $10^{-3.7}$ | N Z Case M |
| 3 day Post Incubation | $10^{-4.3}$ | $10^{-2.5}$ | 250 g/1000 cc |

DOSAGE

The present vaccines stabilized with an effective amount of a casein hydrolysate permit the satisfactory use of these vaccines up to about 35° C while sustaining an activity of a minimum titer or concentration. In the field it is calculated that in a vaccine dosage of 2 ml, about 1 ml will be wasted prior to reaching the tongue and buccal mucosa sites of the fox or other wild carnivore. The remaining dosage is still substantially greater than the minimum immunizing dose of 1 ml of commercial ERA vaccine whose titer of at least $10^{3.4}$ is noted in the prior art Debbie et al., *Am, J. Epid.*, 96(3), 1972, pages 231–235.

TESTING PROCEDURE

Materials

Animals: Red foxes (*Vulpes fulva*) were born and reared in captivity and had no known prior exposure to rabies virus. All foxes were adults (1 year old) and were determined to be serologically negative for rabies antibody before they were included in the test.

Viruses: Two types of modified live rabies vaccine viruses were used in this test procedure. One type, ERA/BHK-21 (ERA virus grown on BHK-21 cells) contained $10^{6.5}$ – $10^{7.3}$ 3-week-old mouse intracerebral $LD_{50's}$($MICLD_{50's}$)/0.03 ml. Another type is PRI virus (ERA virus passed 92 times in porcine kidney $Pk_{2A}$ cells and 46 times in primary canine kidney cells). This virus contained $10^{3.8}$–$10^{4.3}$$MICLD_{50's}$/0.03 ml. The rabies virus used to test or challenge immunity was a suspension of salivary gland tissue from a naturally infected red fox from Alabama. The challenge dose administered to each fox was 160,000 $MICLD_{50's}$ in 0.5 ml volume, 0.25 ml inoculated intramuscularly into each masseter muscle. The diluent was 2% bovine albumin Fraction V containing 100,000 I.U. penicillin and 2.0 mg streptomycin/ml in phosphate buffered water, pH 7.6.

Bait: A preferred bait was prepared from a commercially available meat product cured sausage 12 cm long and 1 cm in diameter. This sausage was "cored" to permit insertion of a plastic tube 11 cm long and 0.5 cm in diameter, and both ends were sealed with rubber plugs. The appropriate vaccine virus (2.0 ml) was inoculated into the plastic tube by inserting a syringe needle through one end plug. 2 ml vaccine was utilized and consideration was given that sufficient vaccine was incorporated in the bait so that the animal is immunized despite a 50% loss.

Methods

The prepared sausage vaccine baits were placed in the individual fox cages and the animals were observed at frequent intervals (about every 10 minutes) until bait was consumed.

EXAMPLE 1

Thirty-nine red foxes were divided into five groups, and every fox in a group was treated as follows:
Protocol:
Group A (7 foxes) — fed 1 bait containing 2.0 ml of ERA/BHK-21 vaccine
Group B (8 foxes) — fed 1 bait containing 2.0 ml of ERA/BHK-21 and 10 weeks later fed a second similar bait
Group C (8 foxes) — fed 1 bait containing 2.0 ml PRI vaccine
Group D (10 foxes) — fed 1 bait containing 2.0 ml PRI vaccine and 10 weeks later fed a second similar bait
Group E (6 foxes) — untreated controls Serologic profiles were constructed on all foxes; these were of 20 weeks duration for foxes that received 1 dose of vaccine and 30 weeks duration for foxes that received 2 doses. Serum neutralizing rabies antibody was measured by the RFFI tissue culture neutralization test. All animals were observed daily for signs of illness or behavioral changes. Foxes were challenged with street rabies virus 21 weeks (foxes fed 1 bait) and 31 weeks (foxes fed 2 baits) after oral vaccination; 6 unvaccinated control foxes were challenged simultaneously.
Results:

All animals were observed for 60 days after the challenge and were then killed. Brain and submaxillary salivary gland tissues from each animal were tested for the presence of infectious rabies virus by standard mouse intracerebral inoculation and fluorescent rabies antibody (FA) tests. Any fox that died during this 60-day observation period or during the postvaccination prechallenge period was similarly examined for rabies.

Temperature stability of the bait with ERA/BHK-21 vaccine was evaluated by holding baits at 4 different temperatures (−20° C, +4° C, +25° C, and +35 ° C) for different periods of time and it was found that a group of baits containing ERA/BHK-21 virus and incorporated N Z amine HD as a stabilizer gave preferred results.
Final Results:

All baits were completely consumed within 2 hours after being placed in the fox cages. Where actual eating of the bait was observed there was some apparent wasting of vaccine as drops of fluid were observed falling from the foxes' mouths. A maximum wastage in all cases did not appear to exceed 1 ml of the 2 ml in the container.

All seven foxes in Group A that received 1 dose of the ERA/BHK-21 bait developed rabies antibody within 2 weeks after vaccination, all had demonstrable antibody at the time of challenge, and all survived the challenge.

Seven of the 8 foxes in Group B that received 2 doses of the ERA/BHK-21 bait developed rabies antibody, five of the seven after the first dose; only one fox never developed demonstrable antibody. One fox which had converted after the second dose of vaccine died on week 15 after vaccination, within hours after surgical removal of a large obstructive urinary calculus. Six of the seven challenged foxes survived; the one death occured in a fox that had never developed antibody.

None of the eight foxes in Group C that received 1 dose of PRI vaccine developed demonstrable antibody, though one of the eight did survive challenge.

All 6 of the Group E control animals died of rabies between 17 and 22 days after challenge.

The stability of the vaccine baits was measured by infectivity of the virus in mice. Depending upon temperature at −20° C or +4° C, the vaccine bait was found to be still potent at 30 days. When stored at +25° C the titer of the vaccine virus fell below acceptable levels sometime between 5 and 10 days and it has been established that the $ED_{50}$ titer of liquid virus using the present type of vaccine delivery for fox immunization is approximately $10^{4.5}$. No significant difference was noted in stability of the vaccines with or without the stabilizer except at 35° C where the stabilizer prolonged vaccine viability.

The results also show in the above groups that the ERA/BHK-21 virus is a more effective immunizing agent than the PRI virus.

The results of the challenge by rabies streed virus demonstrate the value of the antibody as a measure of vaccine efficacy. Of the 33 foxes vaccinated, 21 developed antibody, and of the 20 antibody-positive foxes challenged, 19 survived a massive challenge.

EXAMPLE 2

| Growth Medium and Suspension Medium for Cells | | |
|---|---|---|
| Salts: | | mg/L |
| | NaCl | 6400.0 |
| | KCl | 400.0 |
| | $CaCl_2$ (anhyd.) | 200.0 |
| | $MgSO_4.7H_2O$ | 200.0 |
| | $NaH_2PO_4.H_2O$ | 124.0 |
| | Ferric Nitrate.$9H_2O$ | 0.10 |
| Glucose: | Glucose | 4500.0 |
| Amino Acids: | L-Arginine HCl | 42.0 |
| | L-Cystine | 24.0 |
| | L-Histidine | 16.0 |
| | L-Isoleucine | 52.0 |
| | L-Leucine | 52.0 |
| | L-Lysine HCl | 74.0 |
| | L-Phenylalanine | 33.0 |
| | L-Threonine | 48.0 |
| | L-Tryptophan | 8.0 |
| | L-Tyrosine | 36.0 |
| | L-Valine | 47.0 |
| | L-Methionine | 15.0 |
| | L-Glutamine | 292.0 |
| Vitamins: | Inositol | 3.6 |
| | Choline Cl | 2.0 |
| | Folic acid | 2.0 |
| | Niacinamide | 2.0 |
| | DL-Ca pantothenate | 2.0 |
| | Pyridoxal HCl | 2.0 |
| | Thiamine HCl | 2.0 |
| | Riboflavin | 0.2 |
| | Phenol red | 15.0 |
| Sodium bicarbonate: | $NaHCO_3$ | 22,000 |
| Supplemented with | Tryptose Phosphate Broth | 100 ml/L |
| | 0.1% Bovine serum albumin | |
| | Penicillin | 100 units/ml |
| | Streptomycin | 50 mcg/ml |
| | Amphoterician B | 2 mcg/ml |

We claim:
1. A method of protecting wild carnivores from rabies virus which comprises orally administering to said carnivores an immunizing dose of an attenuated liquid antirabies vaccine containing a temperature stabilizer obtained from a casein hydrolysate, said vaccine being enclosed in a bite-permeable hydrophobic plastic container and said container being surrounded by an acceptable meat bait for said carnivore.
2. The method according to claim 1 wherein the wild carnivore is a fox.

3. The method according to claim 1 wherein the antirabies vaccine is ERA/BHK-21.

4. The method according to claim 1 wherein the antirabies vaccine is PRI virus.

5. The method according to claim 1 wherein the bite-permeable hydrophobic plastic container is an elongated polyethylene tube.

6. The method according to claim 1 wherein said meat bait is an elongated cured sausage.

7. A method of vaccinating wild carnivores against rabies virus which comprises setting out a live attenuated liquid vaccine in bait form in proximity to said carnivore, said bait completely enclosing said attenuated liquid rabies vaccine containing a temperature stabilizer obtained from a casein hydrolysate, said vaccine being further contained in a liquid impermeable plastic container so that teeth penetration by the attracted carnivore will transfer vaccine in immunizing amounts into the buccal mucosa of said carnivore.

8. The method according to claim 7 wherein the wild carnivore is a fox.

9. The method according to claim 7 wherein the live vaccine is ERA/BHK-21.

10. The method according to claim 7 wherein the live vaccine is PRI virus.

11. The method according to claim 7 wherein the liquid impermeable plastic container is an elongated polyethylene tube.

12. The method according to claim 7 wherein the bait is an elongated cured sausage.

13. A vaccine for wild carnivores consisting of an immunizing dose of a liquid attenuated rabies vaccine containing a temperature stabilizer obtained from a casein hydrolysate and said vaccine being contained in a polymeric sheath which is hydrophobic and bite permeable and an acceptable meat bait overcoat surrounding said polymeric sheath.

14. The vaccine according to claim 13 wherein the wild carnivore is a fox.

15. The vaccine according to claim 13 wherein the liquid attenuated rabies vaccine is ERA/BHK-21.

16. The vaccine according to claim 13 wherein the liquid attenuated rabies vaccine is PRI virus.

17. The vaccine according to claim 13 wherein the polymeric sheath is an elongated polyethylene tube.

18. The vaccine according to claim 13 wherein the acceptable meat bait is an elongated cured sausage.

* * * * *